(12) United States Patent
Baker

(10) Patent No.: US 10,520,344 B2
(45) Date of Patent: Dec. 31, 2019

(54) PROPORTIONAL FLOW COMPARATIVE METERING

(71) Applicant: ITRON, INC., Liberty Lake, WA (US)

(72) Inventor: Orion Thomas Baker, Frankfort, KY (US)

(73) Assignee: ITRON, INC., Liberty Lake, WA (US)

( * ) Notice: Subject to any disclaimer, the term of this patent is extended or adjusted under 35 U.S.C. 154(b) by 365 days.

(21) Appl. No.: 15/492,052

(22) Filed: Apr. 20, 2017

(65) Prior Publication Data
US 2018/0306625 A1    Oct. 25, 2018

(51) Int. Cl.
| | | |
|---|---|---|
| G01F 5/00 | (2006.01) | |
| G01F 25/00 | (2006.01) | |
| G01F 1/684 | (2006.01) | |
| G01N 11/04 | (2006.01) | |

(52) U.S. Cl.
CPC ............. *G01F 5/00* (2013.01); *G01F 1/684* (2013.01); *G01F 1/6842* (2013.01); *G01F 25/0007* (2013.01); *G01N 11/04* (2013.01)

(58) Field of Classification Search
CPC .......... G01F 5/00; G01F 1/684; G01F 1/6842; G01F 25/0007; G01N 11/04
See application file for complete search history.

(56) References Cited

U.S. PATENT DOCUMENTS

| | | | | |
|---|---|---|---|---|
| 5,119,672 A | * | 6/1992 | Pfeiffer | F02D 41/187 73/114.34 |
| 5,333,496 A | | 8/1994 | Fenelon | |
| 5,546,801 A | | 8/1996 | Swinson et al. | |
| 5,661,232 A | * | 8/1997 | Van Cleve | G01F 1/8459 73/32 R |
| 5,861,561 A | * | 1/1999 | Van Cleve | G01F 1/8404 73/861.52 |

(Continued)

OTHER PUBLICATIONS

"High Performance Mass Flow Meters and Controllers—800 Series Mass Flow Meters and Controllers," Brochure and Technical Specification, not dated, found at <http://www.sierrainstruments.com/products/pdf/800bro.pdf>, printed on Mar. 8, 2017, Sierra Instruments, Inc., 11 pages.

(Continued)

*Primary Examiner* — Michael J Dalbo

(57) ABSTRACT

A proportional flow meter includes a processor, a measurement channel including a measurement device and a first flow comparison sensor, a bypass channel including a second flow comparison sensor, the measurement and bypass channels operably coupled to an input. The processor may obtain a first measurement from the measurement device and a second measurement from the first flow comparison sensor, where the first and second measurements represent a flow volume of a first portion of a fluid flowing through the measurement channel, and also a third measurement from the second flow comparison sensor, representing a flow volume of a second portion of the fluid flowing through the bypass channel. The processor may determine a ratio of the third measurement to the second measurement, and may determine a total flow volume of the fluid through the measurement and bypass channels collectively based on the first measurement and the determined ratio.

20 Claims, 8 Drawing Sheets

(56) References Cited

U.S. PATENT DOCUMENTS

| | | | | |
|---|---|---|---|---|
| 8,746,032 | B1* | 6/2014 | Feller | G01F 25/0007 |
| | | | | 73/1.35 |
| 9,557,744 | B2 | 1/2017 | Ding | |
| 2004/0216509 | A1* | 11/2004 | Antonijevic | G01F 1/8472 |
| | | | | 73/1.16 |
| 2006/0059985 | A1* | 3/2006 | Seki | G01F 1/6842 |
| | | | | 73/202.5 |
| 2009/0007654 | A1* | 1/2009 | Niikawa | G01F 1/00 |
| | | | | 73/202 |
| 2015/0276449 | A1* | 10/2015 | Ito | G01F 1/78 |
| | | | | 73/861.351 |

OTHER PUBLICATIONS

"Sierra 820 Series Top-TrakTM Mass Flow Meters—Models 820, 820S, 822, 822S, 824, 824S, 826 and 827," Instruction Manual, No. IM-82, Revision E.2, Mar. 2012, copyright Sierra Instruments 2010, 48 pages.

Minehart, Micro Motion, Inc., "Natural Gas Liquid Measurement: Direct and Inferred Mass," White Paper, Emerson Process Management, found at <http://www2.emersonprocess.com/siteadmincenter/PM%20Micro%20Motion%20Documents/Natural-Gas-Liquid-Measurement-Direct-and-Inferred-Mass.pdf>, printed Mar. 8, 2017, copyright 2016, Micro Motion, Inc., 5 pages.

Wang, "Gas-Liquid Two-Phase Flow Rate Measurements by Flow Division and Separation Method," Flow Measurement, Dr. Gustavo Urquiza (Ed.), ISBN: 978-953-51-0390-5, published in print in Mar. 2012, published online on Mar. 28, 2012, pp. 39-72, 35 pages.

\* cited by examiner

US 10,520,344 B2

PROPORTIONAL FLOW COMPARATIVE METERING

FIELD OF THE DISCLOSURE

This disclosure relates generally to fluid flow metering, and more particularly to proportional flow metering.

BACKGROUND

Over time, it has become increasingly important to find less expensive and more efficient ways to conduct flow measurement of fluid (e.g., gas, air, water, other liquids, etc.). One solution involves proportional flow metering, in which a common sized measurement component and/or channel is used along with a bypass channel. Using a bypass channel allows implementations where the maximum flow could or will exceed the capability of the measurement component/channel. Using a proportional flow metering approach, a portion of the fluid bypasses the measurement channel through the bypass channel without being measured, and the total flow is determined as a function of the amount measured in the measurement channel. This proportional flow metering approach is cost effective in that a common sized measurement component/channel can be used across a wide array of sizes or classes of meters, and this can be done regardless of the specific measurement technology (e.g., type of measurement device(s)) used. In utility metering, for example, smaller residential measurement modules may be utilized outside of their designed range of operation, such as in commercial or industrial metering, saving money by using common parts across product lines. A further potentially cost effective approach is static metering, which may be used in conjunction with proportional flow metering. Static metering is increasingly becoming a prevalent solution for fluid metering for a variety of reasons. With static metering, sensors are used to determine fluid flow measurements instead of moving parts (e.g., diaphragms, turbines, pistons, etc.), which not only reduces initial total part cost, but also greatly reduces the cost of repair of failing parts.

When using proportional flow metering implementations (with or without static metering), however, a variety of physical factors (e.g., pressure, density, temperature, pre-meter conditioning, piping configuration, etc.) can affect the accuracy of the total flow measurement. These physical and/or environmental inconsistencies in the measurement and bypass channels may result in an inaccurate determination of total fluid flow volume. In an attempt to avoid this, some implementations use strict conditioning of fluidics of a meter (e.g., physically altering flow via pipe layout or use of devices placed in the meter and/or flow channel to alter flow effects), and/or try to exactly replicate a flow path into identical channels to attain as consistent conditions as possible. Thus, a number of design constraints may be placed on designs looking to utilize a proportional flow implementation. Even so, these approaches still do not guarantee accurate ratio determination across a wide array of installation applications and variables.

Figure 1:
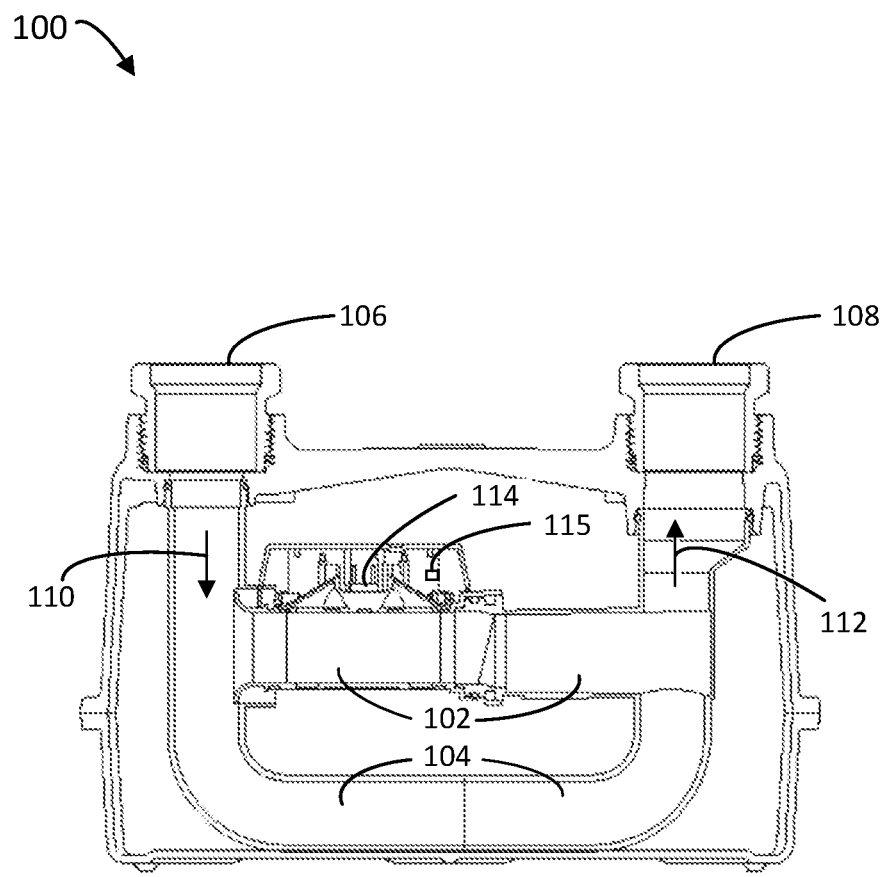
FIG. 1 is an illustration of a proportional flow meter.

In the drawings, the leftmost digit(s) of a reference number may identify the drawing in which the reference number first appears.

DETAILED DESCRIPTION

In order to lower fluid metering solution costs while providing improved accuracy in collected data, a way of providing more accurate total flow measurements from a proportional flow metering device is needed. The following description discloses a proportional flow metering solution in which low-cost sensors or other measurement means may be used to provide more accurate fluid flow volume data while being able to continue to employ a common sized measurement module (a typically expensive portion of a meter) in a wide range of fluid metering implementations that may be exposed to a wide variety of physical and/or environmental variables. As used herein, the term "fluid" may refer to any gas (e.g., air, natural gas, nitrogen, helium, argon, oxygen, or any gas) or liquid (e.g., water, gasoline, oil, or any liquid).

Embodiments are now described with reference to the figures, where like reference numbers may indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the description. It will be apparent to a person skilled in the relevant art that the technology disclosed herein can also be employed in a variety of other systems and applications other than what is described herein.

FIG. 1 is an illustration of a proportional flow meter 100 as may be commonly known for utility metering of fluids such as gases or liquids. Proportional flow meter 100 may include a measurement channel 102 and a bypass channel 104. Proportional flow meter 100 may also include an input 106 and an output 108, both shared by measurement channel 102 and bypass channel 104. In an example, a fluid may enter proportional flow meter 100 at input 106 and flow in the direction of arrow 110. A first portion of the fluid may flow through measurement channel 102, while a second portion of the fluid may flow through bypass channel 104. The fluid may then recombine and exit proportional flow meter 100 at output 108 in the direction of arrow 112. As the first portion of the fluid passes through measurement channel 102, a measurement device 114 may take a measurement representative of a flow volume of the first portion of the fluid passing through measurement channel 102. Measurement device 114 may include any type of fluid flow measurement device, including, but not limited to, a sensor (e.g., a pressure sensor, a thermal sensor, a mass air flow sensor, an optical flow sensor, an ultrasonic sensor, etc.), a mechanical measurement device or positive displacement device (e.g., a rotary metering device, a diaphragm metering device, a piston metering device, a gear metering device, a disk metering device, a turbine metering device, a jet metering device, a vortex metering device, etc.), etc., as would be known by those of ordinary skill in the art, as well as any future developed fluid flow measurement devices or means.

A processor 115 in direct or indirect communication with measurement device 114 (e.g., via wired and/or wireless communications, a bus, or other means of passing communications or data) may determine the flow volume of the fluid passing through measurement channel 102 based on the measurement taken and provided to processor 115 by measurement device 114. For example, measurement device 114 may measure a resistance, a voltage, a current, etc., that is representative of a flow volume of the fluid passing through measurement channel 102. That measurement may be provided to processor 115, and used by processor 115 to determine a flow volume of the fluid passing through measurement channel 102. The determined flow volume of the fluid passing through measurement channel 102 may then be used by processor 115, or another processor internal or external to meter 100, to determine a total flow volume of proportional flow meter 100. An example of a total flow volume determination is further described with reference to FIG. 2.

Figure 2:
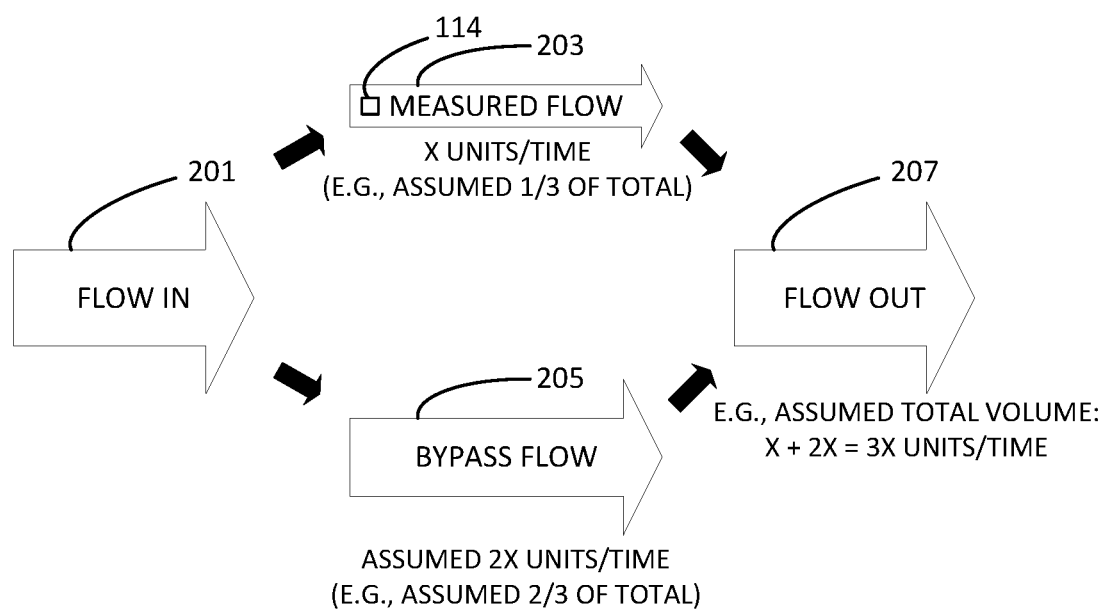
FIG. 2 is a diagram showing flow measurement and an example of total flow determination of a proportional flow meter, such as the proportional flow meter shown in FIG. 1.

FIG. 2 is a diagram showing flow measurement and an example of total flow determination of a proportional flow meter, such as proportional flow meter 100 shown in FIG. 1. Referring to both FIGS. 1 and 2 for purposes of example, a fluid flow, as depicted by arrow 201, may flow into proportional flow meter 100 via input 106, and assumed proportionally divided between measurement channel 102 (as depicted by arrow 203) and bypass channel 104 (as depicted by arrow 205). In the example shown, the proportion of the flow in bypass channel 104 to the flow in measurement channel 102 is shown assumed to be 2 to 1. In other words, in this example, it is assumed that twice the fluid flows through bypass channel 104 than flows through measurement channel 102. In measurement channel 102, a measurement may be taken by measurement device 114 that is representative of the flow volume of a first portion of the fluid flowing through measurement channel 102. The measurement may be provided to processor 115, or another processor, which may then determine, based on the provided measurement, that the flow volume of the fluid passing through measurement channel 102 is X units/time (e.g., kilograms per second, liters per hour, gallons per minute, British Thermal Units (BTU) per hour, cubic meters per hour, cubic feet per minute, cubic feet per hour, etc.). For simplicity of example, consider a determination of 3.33 cubic feet per minute of a gas flowing through measurement channel 102. The first portion of the fluid flowing through measurement channel 102 and a second portion of the fluid flowing through bypass channel 104 recombine and exit proportional flow meter 100 via output 108 (as depicted by arrow 207). Based on the assumed proportional division of the flow (in this example, 2 to 1), processor 115, or another processor, may determine the collective flow of fluid that entered/exited proportional flow meter 100 to be X+2X=3X units/time. In our numerical example, this would be 3.33+2(3.33)=9.99 cubic feet per minute (or approximately 600 cubic feet per hour). However, this total flow volume determination is based on an assumed proportional division of the flow, which may be inaccurate in itself, but also may be further inaccurate based on the various physical and/or environmental factors that may affect the fluid in a variable manner (as discussed above) that cannot be easily taken into account.

Figure 3:
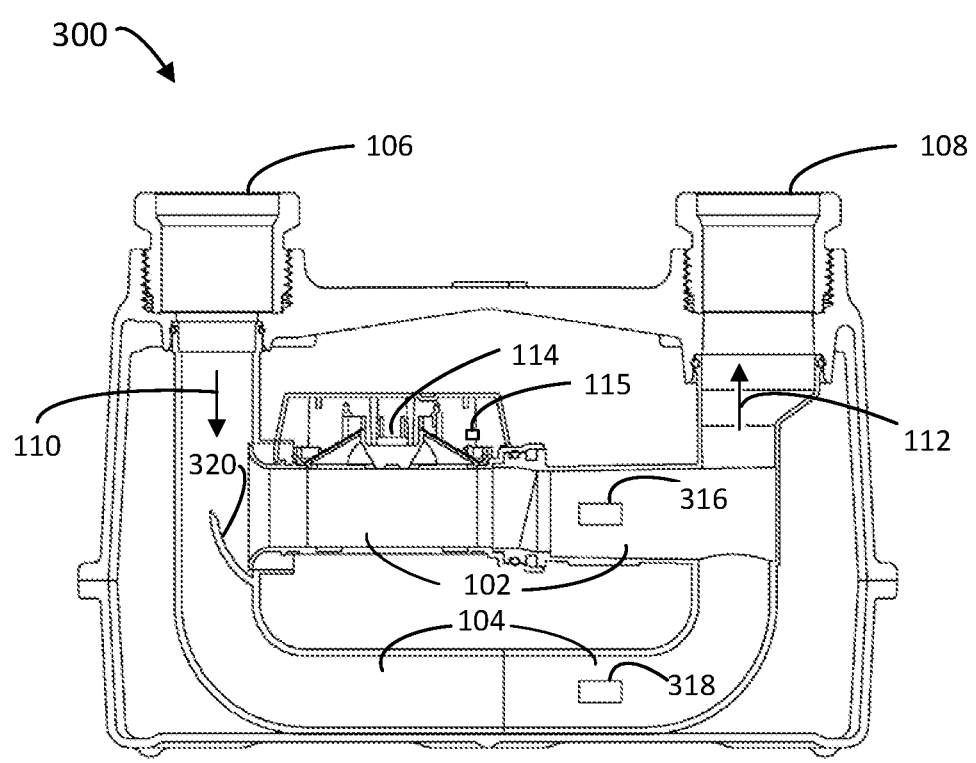
FIG. 3 is an illustration of a proportional flow meter configured for use with proportional flow comparison, according to embodiments of the present disclosure.

FIG. 3 is an illustration of a proportional flow meter 300 configured for use with proportional flow comparison, according to embodiments of the present disclosure. Proportional flow meter 300 is similar to proportional flow meter 100 of FIG. 1, but further includes a first flow comparison sensor 316 disposed within measurement channel 102 and a second flow comparison sensor 318 disposed within bypass channel 104. First and second flow comparison sensors 316 and 318 may include any type of fluid flow measurement device, including, but not limited to, a pressure sensor, a thermal sensor, a mass air flow sensor, an optical flow sensor, an ultrasonic sensor, etc., as would be known by those of ordinary skill in the art, as well as any future developed fluid flow measurement devices or means. A mechanical measurement device (e.g., a rotary metering device, a diaphragm metering device, a piston metering device, a gear metering device, a disk metering device, a turbine metering device, a jet metering device, a vortex metering device, etc.) may also be used as a flow comparison measurement device, though may not be as compact, and would not typically be used in a static flow measurement device implemented to avoid the use of movable parts. The first flow comparison sensor 316 and second flow comparison sensor 318 may be placed or mounted in their respective channels on a wall of the channel, on a post placed into the channel, on a wire strung in or across the channel, etc., as would be understood by one of ordinary skill in the relevant art.

The first flow comparison sensor 316 and second flow comparison sensor 318 may be the same or similar type (e.g., same type, make, model, etc.) of sensor, or may be different types of sensors, with similar calibration. For more accurate results, first flow comparison sensor 316 and second flow comparison sensor 318 may be paired to be within a tolerance of each other (e.g., within X.XX micro ohms of each other), or calibrated to be within a tolerance of accuracy in reference to each other.

Proportional flow meter 300 may optionally include a conditioning geometry, such as protrusion 320, which may help guide or direct the flow of fluid into measurement channel 102 and bypass channel 104.

Figure 4:
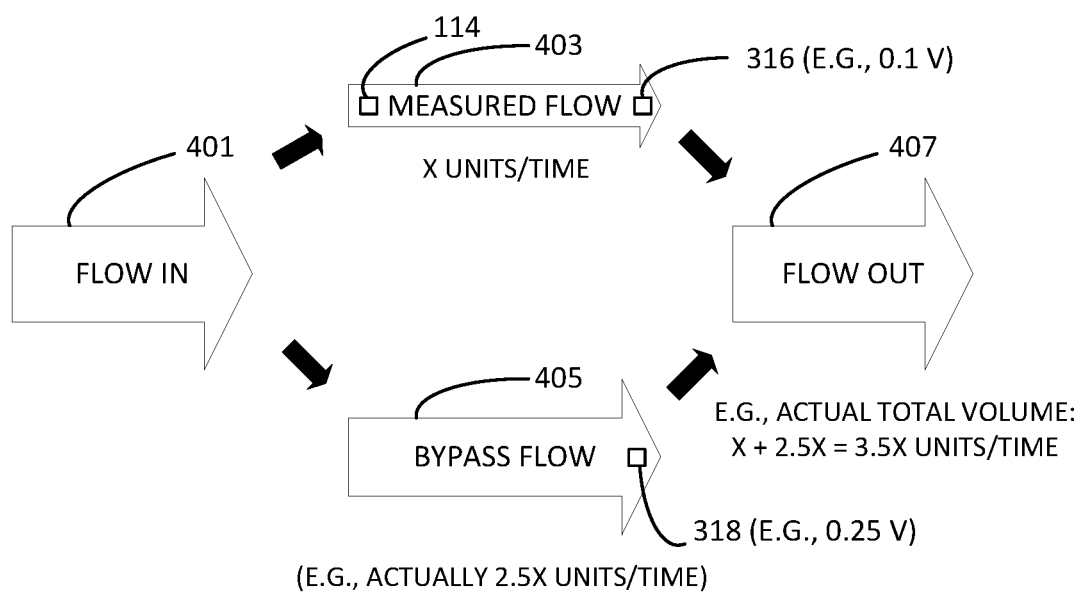
FIG. 4 is a diagram showing flow measurement and example total flow determination of a proportional flow meter, such as the proportional flow meter shown in FIG. 2, according to embodiments of the present disclosure.

FIG. 4 is a diagram showing flow measurement and an example of total flow determination of a proportional flow meter, such as proportional flow meter 300 shown in FIG. 3, according to embodiments of the present disclosure. Referring to both FIGS. 3 and 4 for purposes of example, a fluid flow, as depicted by arrow 401, may flow into proportional flow meter 300 via input 106, and may be proportionally divided between measurement channel 102 (as depicted by arrow 403) and bypass channel 104 (as depicted by arrow 405). Different from the example described with reference to FIG. 2, in the example shown in FIG. 4, the proportion of the flow in bypass channel 104 to the flow in measurement channel 102 is not assumed. The determination of the proportion of the flow in bypass channel 104 will now be described.

In measurement channel 102, a measurement may be taken by measurement device 114 that is representative of the flow volume of a first portion of the fluid flowing through measurement channel 102. A second measurement may be taken by first flow comparison sensor 316 that is also representative of the flow volume of the first portion of the fluid flowing through measurement channel 102. A third measurement may be taken by second flow comparison sensor 318 that is representative of the flow volume of a second portion of the fluid flowing through bypass channel 104. Processor 115, and/or optionally one or more other processors internal or external to meter 300 (e.g., inside index housing of meter 300 or remote from meter 300) (not shown in FIG. 3 or 4), may each be directly or indirectly in communication with at least one of measurement device 114, first flow comparison sensor 316, and second flow comparison sensor 318 (e.g., via wired and/or wireless communications, a bus, or other means of passing communications or data), and may be provided with the first, second, and third measurements. Rather than assume the proportion of the flow volume of the second portion of the fluid flowing through bypass channel 104 to the flow volume of the first portion of the fluid flowing through measurement channel 102, processor 115, or another processor, may determine the proportion based on the second and third measurements. For example, consider a second measurement of 0.1 V as taken by first flow comparison sensor 316 in measurement channel 102 and a third measurement of 0.25 V as taken by second flow comparison sensor 318 in bypass channel 104. Processor 115 may determine the proportion of the flow volume of the second portion of the fluid flowing through bypass channel 104 to the flow volume of the first portion of the fluid flowing through measurement channel 102 to be 0.25V/0.1V, or 2.5 to 1, which may be a more accurate determination of the proportion than simply assuming the proportion, especially if any physical or environmental factors are present that may affect fluid flow through proportional flow meter 300. In an alternative embodiment, processor 115, or another processor, may determine respective actual flow volumes though each channel based on the second and third measurements, and use the determined actual flow volumes to determine the proportion of the flow volume in bypass channel 104.

The determination of the proportion of the flow in bypass channel 104 will now be described with reference to FIGS. 3 and 4. Based on the first measurement provided by measurement device 114, processor 115, or another processor, may determine that the flow volume of the fluid passing through measurement channel 102 is X units/time. For simplicity of example, consider a determination of 3.3 cubic feet per minute of a gas flowing through measurement channel 102. The first portion of the fluid flowing through measurement channel 102 and the second portion of the fluid flowing through bypass channel 104 recombine and exit proportional flow meter 300 via output 108 (as depicted by arrow 407). Based on the determined flow volume through measurement channel 102 and the determined proportion, processor 115, or another processor, may determine the collective flow volume of fluid that entered/exited proportional flow meter 300 to be X+2.5X=3.5X units/time. In our numerical example, this would be 3.3+2.5(3.3)=11.55 cubic feet per minute, or 693 cubic feet per hour, which may be more accurate than the total flow volume determined in the prior art example depicted by FIGS. 1 and 2 (determined to be 9.99 cubic feet per minute, or approximately 600 cubic feet per hour), which was based on an assumed proportion of the flow volume in bypass channel 104, rather than a determined proportion.

Figure 5:
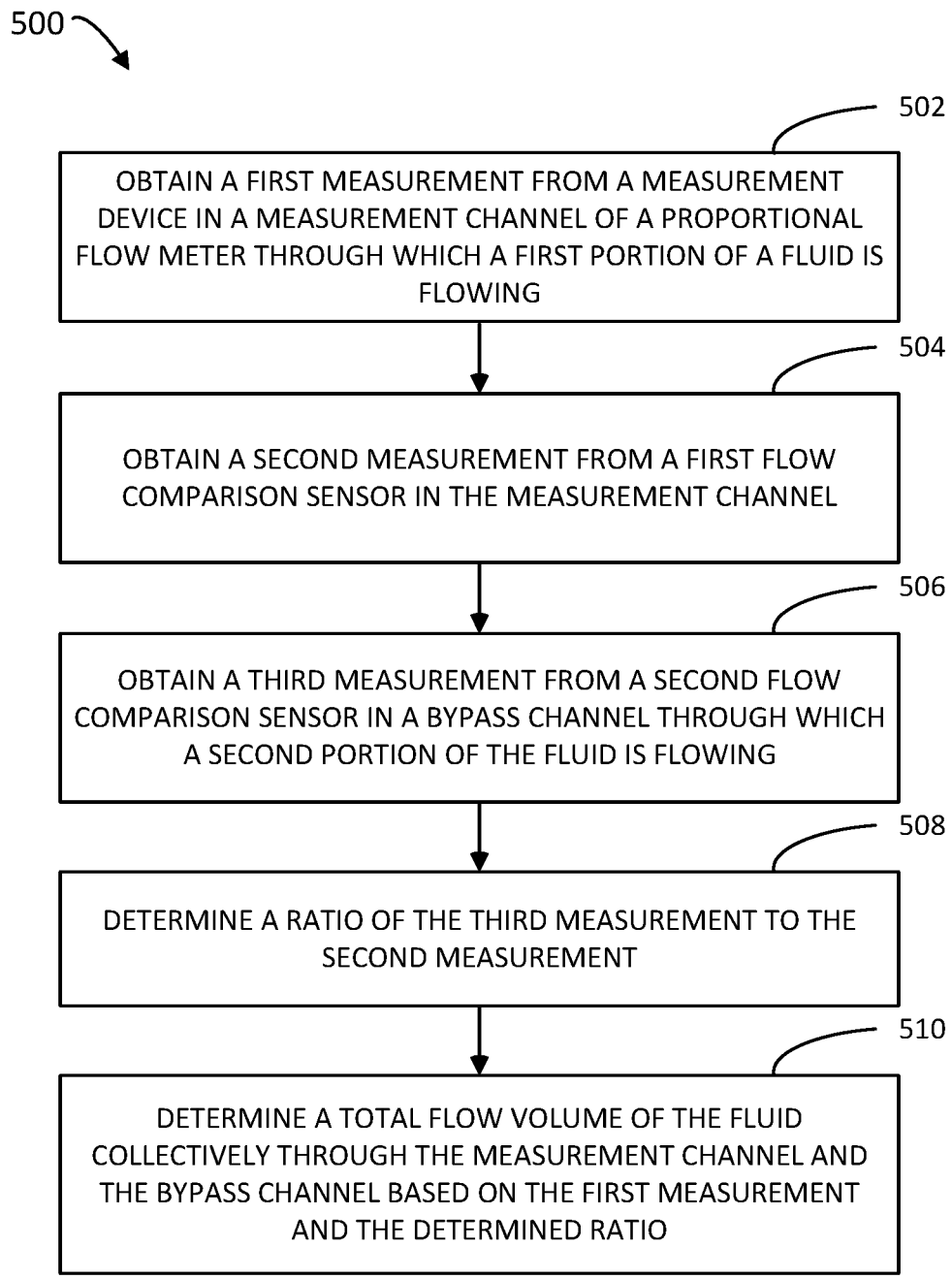
FIG. 5 is a flow diagram of an example proportional flow measurement process, according to embodiments of the present disclosure.

FIG. 5 is a flow diagram of an example proportional flow measurement process 500, according to embodiments of the present disclosure. Process 500 summarizes the determination of total flow volume through a proportional flow meter, as was described above with reference to FIGS. 3 and 4. At 502, a first measurement may be obtained (e.g., received by a processor) from a measurement device in a measurement channel of a proportional flow meter through which a first portion of a fluid is flowing. The first measurement may be representative of the flow volume of the first portion of the fluid flowing through the measurement channel. At 504, a second measurement may be obtained from a first flow comparison sensor in the measurement channel. The second measurement may also be representative of the flow volume of the first portion of the fluid flowing through the measurement channel. At 506, a third measurement may be obtained from a second flow comparison sensor in a bypass channel of the proportional flow meter through which a second portion of the fluid is flowing. The third measurement may be representative of the flow volume of the second portion of the fluid flowing through the bypass channel. At 508, the processor may determine a ratio of the third measurement to the second measurement. At 510, a total flow volume of the fluid collectively through the measurement channel and the bypass channel may be determined by the processor based on the first measurement and the determined ratio.

Referring back to FIGS. 3 and 4, while one bypass channel 104 is shown and described, further embodiments may include additional bypass channels. In those embodiments, each bypass channel may include a respective flow comparison sensor, and the proportion ratios for each bypass channel may be determined and used to determine a total flow volume of fluid collectively through the measurement channel and the bypass channel(s), as would be understood by one of ordinary skill in the art after reading this disclosure.

Again referring to FIGS. 3 and 4, in an embodiment, first flow comparison sensor 316 may not need to be present. In such an embodiment, the measurement provided by measurement device 114 may be used in place of the measurement that would have been provided by first flow comparison sensor 316 to determine the proportion ratio in the above described example. In this embodiment, it would be important for measurement device 114 to be able to be accurately calibrated to correspond to (or be within a given tolerance of) the calibration of flow comparison sensor 318.

Figure 6:
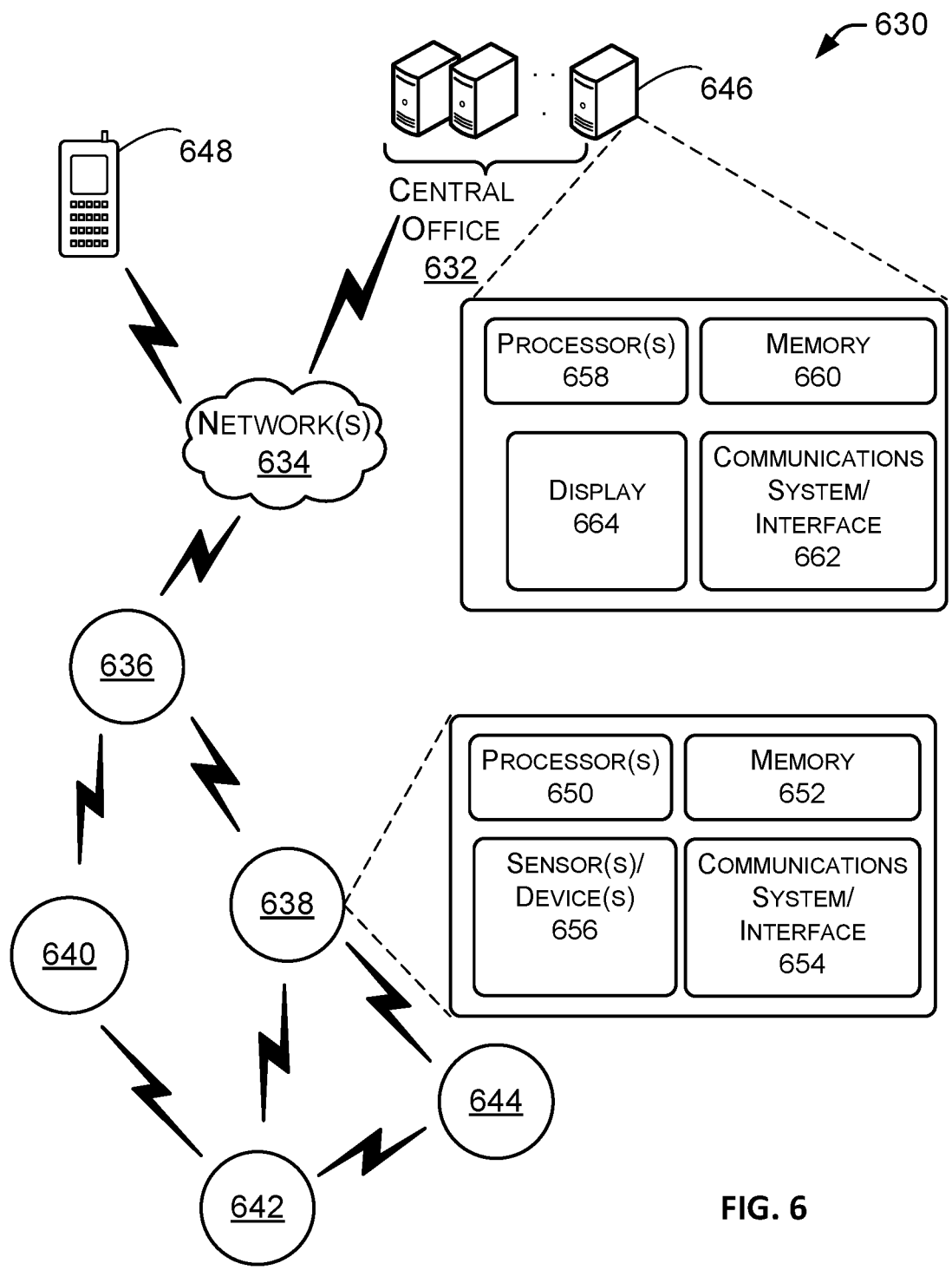
FIG. 6 is an illustration of a network environment in which example methods, apparatus, and articles of manufacture disclosed herein may be implemented, according to embodiments of the present disclosure.

Proportional flow meter 300 of FIG. 3 may be a part of an advanced meter reading (AMR) network or an advanced metering infrastructure (AMI) network, such as data collection network 630 of FIG. 6, according to embodiments. Data collection network 630 may include a central office 632, which may be associated with a data collection/processing entity (e.g., a utility company). The central office may communicate with network nodes through one or more networks 634, which may be the Internet or other network having widespread or local functionality. Network nodes may include nodes 636-644, which may include, for example, endpoint devices such as utility meters or other devices that may comprise sensors, actuators, etc. (e.g., fluid flow measurement devices, gas meters, water meters, etc.). These nodes may be located at various locations (e.g., homes, businesses, etc.). Nodes 636-644 may be configured in a mesh network, star network or other configuration. One or more of the network nodes (e.g., device 636) may be a data collector and/or concentrator that may be configured for communication (e.g., radio frequency (RF) communication, cellular communication, etc.) with a plurality of downstream nodes 638-644, which may also be configured for similar communications. In an example operation, data collector 636 may receive data or other communications from nodes 638-644 to be provided to a data collection device 646, (which may be located at central office 632) and/or a mobile data collection device 648, and/or vice versa. For example, in an AMR or AMI network, the collected data may include consumption data or other information associated with a utility meter (e.g., a gas meter, a water meter, etc.). Additionally, data collector 636 may send software updates, firmware updates, instructions or other information (which may have been communicated to data collector 636 from data collection device 646 or 648, for example) to one or more of the nodes 638-644. In an embodiment, one or more network nodes (e.g., nodes 636-644) may be powered by a battery.

In an expanded view, data collection device 646 (and/or mobile data collection device 648) may include, among other components, one or more controllers or processors 658, a memory 660, a communication system and/or interface 662 (e.g., configured for RF communications, cellular communications, or another type of communications), and optionally a display 664. Nodes 636-644 may include, among other components, one or more controllers or processors 650, a memory 652, a communication system and/or interface 654 (e.g., configured for RF communications, cellular communications, or another type of communications), and one or more sensors/devices 656, which may include, for example, one or more measurements sensors/devices, a first flow comparison sensor, a second flow comparison sensor, etc., described above with reference to FIGS. 3 and 4. Processor(s) 650 of the network nodes and/or processor(s) 658 of the data collection devices 646 and/or 648 may assume the role of processor(s) 115 described above with reference to FIGS. 3 and 4.

One or more features disclosed herein may be implemented in hardware, software, firmware, and/or combinations thereof, including discrete and integrated circuit logic, application specific integrated circuit (ASIC) logic, and microcontrollers, and may be implemented as part of a domain-specific integrated circuit package, or a combination of integrated circuit packages. The terms software and firmware, as used herein, refer to a computer program product including at least one computer readable medium having computer program logic, such as computer-executable instructions, stored therein to cause a computer system to perform one or more features and/or combinations of features disclosed herein. The computer readable medium may be transitory or non-transitory. An example of a transitory computer readable medium may be a digital signal transmitted over a radio frequency or over an electrical conductor, through a local or wide area network, or through a network such as the Internet. An example of a non-transitory computer readable medium may be a compact disk, a flash memory, SRAM, DRAM, a hard drive, a solid state drive, or other data storage device.

A processing platform of a data collection device (e.g., data collection device 646 or mobile data collection device 648 of FIG. 6), and/or a metering device (e.g., any of devices 636-644) may be embodied in any type of mobile and/or non-mobile computing device. Examples of mobile devices may include, but are not to be limited to, laptop computers, ultra-laptop computers, tablets, touch pads, portable computers, handheld computers, palmtop computers, personal digital assistants (PDAs), e-readers, cellular telephones, combination cellular telephone/PDAs, mobile smart devices (e.g., smart phones, smart tablets, etc.), mobile internet devices (MIDs), mobile messaging devices, mobile data communication devices, mobile media playing devices, cameras, mobile gaming consoles, wearable devices, mobile industrial field devices, etc. Examples of non-mobile devices may include, but are not to be limited to, servers, personal computers (PCs), Internet appliances, televisions, smart televisions, data communication devices, media playing devices, gaming consoles, industrial field devices, etc.

Figure 7:
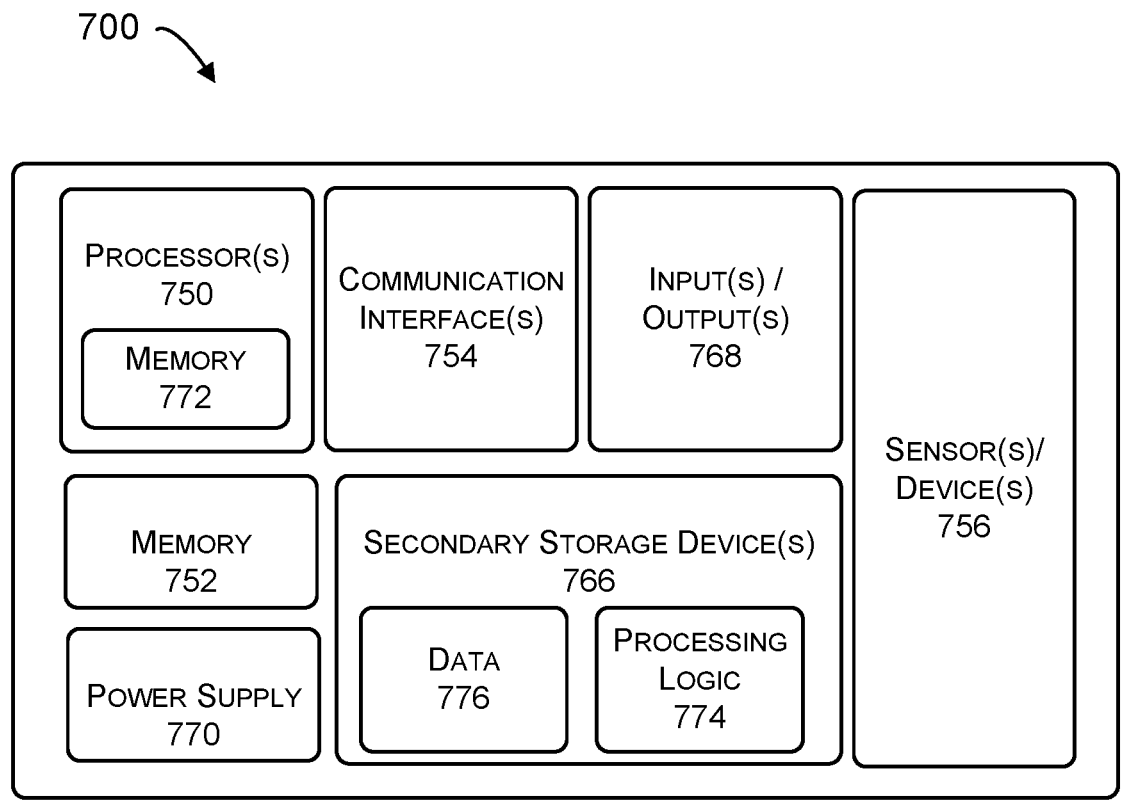
FIG. 7 is a block diagram showing various components of an example processing platform of a fluid flow measurement device (e.g. a metering device), according to an embodiment of the present disclosure.

FIG. 7 is a block diagram of an example processing platform 700 of a metering device, according to embodiments. Processing platform 700 may include one or more processors 750, memory 752, one or more secondary storage devices 766, one or more input/output devices 768, and/or one or more communication interfaces 754, in communication via a bus, line, or similar implementation (not shown). Processing platform 700 may also include a power supply 770, which may include an interface to an electricity source and/or may include one or more batteries. Platform 700 may also include one or more sensors/devices 756, that may include, for example, at least one measurement device, a first flow comparison sensor, a second flow comparison sensor, etc.

Processor(s) 750 may be implemented by, for example but not limitation, one or more integrated circuits, logic circuits, microprocessors, controllers, etc. Processor(s) 750 may include a local memory 772 (e.g., a cache). Memory 752 may include a volatile and/or a non-volatile memory. Volatile memory may be implemented by, for example but not limitation, Synchronous Dynamic Random Access Memory (SDRAM), Dynamic Random Access Memory (DRAM), and/or any other type of random access memory device. Non-volatile memory may be implemented by flash memory and/or any other desired type of memory device. Access to memory 752 may be controlled by a memory controller (not shown). Data stored in memory 752 and/or local memory 772 may be used by processor(s) 750 to facilitate sensor data collection functions, metering functions and/or metering calculations/computations if embodied in a utility meter, and/or communications, etc., according to embodiments of this disclosure.

Input/output device(s) 768 may allow a user to interface with processor(s) 750. Input devices may allow a user to enter data and/or commands for processor(s) 750. Input devices may include, for example, an audio sensor, a microphone, a camera (e.g., still, video, etc.), a keyboard, a button, a mouse, a touchscreen, a track-pad, a trackball, isopoint, a voice recognition system, etc. Output devices may provide or present information to a user. Output devices may include, for example, display devices (e.g., a light emitting diode (LED), an organic light emitting diode (OLED), a liquid crystal display, a cathode ray tube display (CRT), a touchscreen, a tactile output device, a printer, speakers, etc.). The input/output device(s) 768 may be connected to processor(s) 750, for example, with an interface circuit (not shown). The interface circuit may be implemented by any type of interface standard, such as, for example, an Ethernet interface, a universal serial bus (USB), a PCI express interface, etc. For use with an output device, the interface circuit may include a graphics driver card, chip, and/or processor.

Communication interface(s) 754 may be implemented in hardware or a combination of hardware and software, and may provide wired or wireless network interface(s) to one or more networks, such as network(s) 634 of FIG. 6. Communication interface(s) 754 may be a part of, or connected with, the interface circuit discussed above, and/or may include or connect with communication devices such as a transmitter, a receiver, a transceiver, a modem and/or network interface card to facilitate exchange of data with external devices via a network, such as network(s) 634. In an embodiment, security mechanisms may be used to provide secure communications, as would be understood by one of ordinary skill in the art.

Secondary storage device(s) 766 may store processing logic 774 (e.g., software) to be executed by processor(s) 750, and/or may store data 776. Processing logic 774 and data 776 may be used by processor(s) 750 to facilitate sensor data collection functions, metering functions and/or metering calculations/computations if embodied in a utility meter, and/or communications between devices, etc., according to embodiments of this disclosure. Processing logic 774 may include instructions for executing the methodology described herein for a proportional flow measurement device, for example. Examples of secondary storage device(s) 766 may include one or more hard drive disks, compact disk (CD) drives, digital versatile disk (DVD) drives, Blu-ray disk drives, redundant array of independent disks (RAID) systems, floppy disk drives, flash drives, etc. Data and/or processing logic may be stored on a removable tangible computer readable storage medium (e.g., a floppy disk, a CD, a DVD, a Blu-ray disk, etc.) using one or more of the secondary storage device(s) 766.

Figure 8:
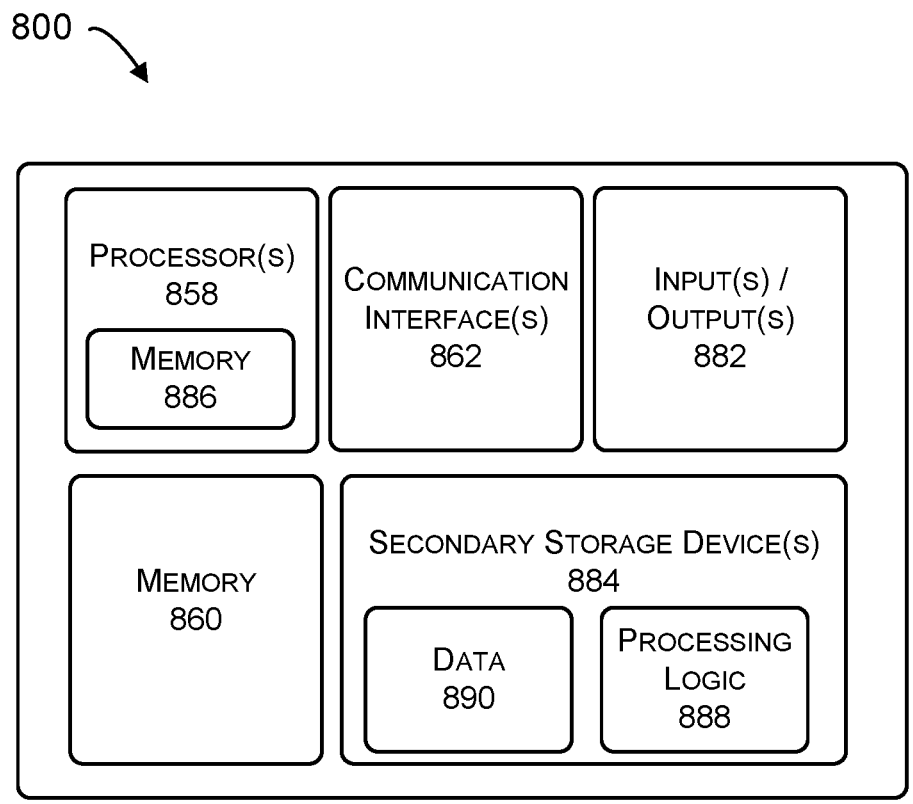
FIG. 8 is a block diagram of an example processing platform of a data collection device, according to an embodiment of the present disclosure.

FIG. 8 is a block diagram of an example processing platform 800 of a mobile or non-mobile data collection device, according to embodiments. Processing platform 800 may include one or more processors 858, memory 860, one or more secondary storage devices 884, one or more input/output devices 882, and/or one or more communication interfaces 862, in communication via a bus, line, or similar implementation (not shown). Processing platform 800 may also include a power supply (not shown), which may include an interface to an electricity source and/or may include one or more batteries.

Processor(s) 858 may be implemented by, for example but not limitation, one or more integrated circuits, logic circuits, microprocessors, controllers, etc. Processor(s) 858 may include a local memory 886 (e.g., a cache). Memory 860 may include a volatile and/or a non-volatile memory. Volatile memory may be implemented by, for example but not limitation, Synchronous Dynamic Random Access Memory (SDRAM), Dynamic Random Access Memory (DRAM), and/or any other type of random access memory device. Non-volatile memory may be implemented by flash memory and/or any other desired type of memory device. Access to memory 860 may be controlled by a memory controller (not shown). Data stored in memory 860 and/or local memory 886 may be used by processor(s) 858 to facilitate data collection functions and/or communications, metering calculations/computations (e.g., if not done at the metering device(s)), etc., according to embodiments of this disclosure.

Input/output device(s) 882 may allow a user to interface with processor(s) 858. Input devices may allow a user to enter data and/or commands for processor(s) 858. Input devices may include, for example, an audio sensor, a microphone, a camera (e.g., still, video, etc.), a keyboard, a button, a mouse, a touchscreen, a track-pad, a trackball, isopoint, a voice recognition system, etc. Output devices may provide or present information to a user. Output devices may include, for example, display devices (e.g., a light emitting diode (LED), an organic light emitting diode (OLED), a liquid crystal display, a cathode ray tube display (CRT), a touchscreen, a tactile output device, a printer, speakers, etc.). The input/output device(s) 882 may be connected to processor(s) 858, for example, with an interface circuit (not shown). The interface circuit may be implemented by any type of interface standard, such as, for example, an Ethernet interface, a universal serial bus (USB), a PCI express interface, etc. For use with an output device, the interface circuit may include a graphics driver card, chip, and/or processor.

Communication interface(s) 862 may be implemented in hardware or a combination of hardware and software, and may provide wired or wireless network interface(s) to one or more networks, such as network(s) 634 of FIG. 6. Communication interface(s) 862 may be a part of, or connected with, the interface circuit discussed above, and/or may include or connect with communication devices such as a transmitter, a receiver, a transceiver, a modem and/or network interface card to facilitate exchange of data with external devices via a network, such as network(s) 634. In an embodiment, security mechanisms may be used to provide secure communications, as would be understood by one of ordinary skill in the art.

Secondary storage device(s) 884 may store processing logic 888 (e.g., software) to be executed by processor(s) 858, and/or may store data 890. Processing logic 888 and data 890 may be used by processor(s) 858 to facilitate data collection functions and/or communications between devices, metering calculations/computations (e.g., if not done at the metering device(s)), etc., according to embodiments of this disclosure. Processing logic 888 may include instructions for executing the methodology described herein for a data collection device, for example. Examples of secondary storage device(s) 884 may include one or more hard drive disks, compact disk (CD) drives, digital versatile disk (DVD) drives, Blu-ray disk drives, redundant array of independent disks (RAID) systems, floppy disk drives, flash drives, etc. Data and/or processing logic may be stored on a removable tangible computer readable storage medium (e.g., a floppy disk, a CD, a DVD, a Blu-ray disk, etc.) using one or more of the secondary storage device(s) 884.

The embodiments described herein involving comparative measurement provide an improved proportional fluid flow measurement system that measures the proportion of a fluid between a measurement channel and a bypass channel, rather than assuming the proportion. This provides a more accurate determination of total flow volume, even in variable physical and environmental conditions, and can provide a real-time adjustment with changes of such conditions. Comparative measurement allows a greater freedom of design, allowing more cost efficient and compact arrangements, which is especially important in instances where strict conditioning or replication of flow paths is infeasible or inefficient. In addition to the known cost-savings of using a proportional flow system that allows a common-sized measurement component/channel to be used across a wide array of implementations, the flow comparison sensor(s) (or other comparative measurement means) used in the improved system may be inexpensive (e.g., as compared to the primary measurement device used), as they are used to determine proportion and not for actual flow measurement.

The particular examples used in this document are for ease of understanding and are not to be limiting. Though described for use with utility metering (e.g., of gas, water, etc.), features described herein may be used in many other contexts that may or may not involve utility metering. The improved accuracy and cost-saving features discussed herein may be beneficial in many other systems involving measurement of fluid flow volume, including fields yet unknown, where accurate measurement of large volumes of fluid flow is required with minimal measurement investment.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A proportional flow meter for measuring volume flow of a fluid, comprising:
   an input through which the fluid flows;
   a processor;
   a measurement channel operably coupled to the input, the measurement channel including a measurement device and a first flow comparison sensor, each in communication with the processor; and
   a bypass channel operably coupled to the input, the bypass channel including a second flow comparison sensor in communication with the processor;
   wherein the processor is configured to:
      receive a first measurement from the measurement device, the first measurement representative of a flow volume amount of a first portion of the fluid flowing through the measurement channel from the input;
      receive a second measurement from the first flow comparison sensor, the second measurement representative of a first comparison flow volume amount of the first portion of the fluid flowing through the measurement channel from the input;
      receive a third measurement from the second flow comparison sensor, the third measurement representative of a second comparison flow volume amount of a second portion of the fluid flowing through the bypass channel from the input;
      determine a ratio of the third measurement to the second measurement; and
      determine a total flow volume of the fluid based on the first measurement and the determined ratio.

2. The proportional flow meter of claim 1, wherein the first flow comparison sensor and the second flow comparison sensor are the same type of sensor.

3. The proportional flow meter of claim 1, wherein the first flow comparison sensor and the second flow comparison sensor are each calibrated to be within a tolerance of accuracy in reference to each other.

4. The proportional flow meter of claim 1, wherein the processor is configured to determine the total flow volume of the fluid based on the first measurement and the determined ratio according to the following formula:

$$\text{Total Flow Volume} = X + X(Z/Y);$$

wherein:
X is the flow volume amount of the fluid based on the first measurement;
Y is the second measurement; and
Z is the third measurement.

5. The proportional flow meter of claim 1, further comprising:
   a conditioning geometry at the input to guide the first portion of the fluid into the measurement channel and to guide the second portion of the fluid into the bypass channel.

6. The proportional flow meter of claim 1, wherein the fluid is a gas.

7. The proportional flow meter of claim 1, wherein the fluid is a liquid.

8. The proportional flow meter of claim 1, further including a housing.

9. The proportional flow meter of claim 8, wherein the processor is located within the housing.

10. The method of claim 9, wherein the fluid is a gas or a liquid.

11. The proportional flow meter of claim 8, wherein the processor is located external to the housing, and wherein the proportional flow meter further comprises:
    a communications subsystem for providing measurement data to the processor over a network.

12. A method of measuring fluid flow in a proportional flow device through which a flow of fluid is divided between at least two flow channels, the method comprising:
    disposing a measurement device in a first channel of a proportional flow device;
    disposing a first flow comparison sensor in the first channel of the proportional flow device;
    disposing a second flow comparison sensor in a second channel of the proportional flow device, the second channel acting as a bypass channel, and the first and second channels sharing an input;
    obtaining a first measurement from the measurement device in the first channel through which a first portion of a fluid is flowing, the first measurement representative of a flow volume amount of the fluid flowing through the first channel;
    obtaining a second measurement from the first flow comparison sensor in the first channel, the second measurement representative of a first comparison flow volume amount of the fluid flowing through the first channel;
    obtaining a third measurement from the second flow comparison sensor in the second channel through which a second portion of the fluid is flowing, the third measurement representative of a second comparison flow volume amount of the fluid flowing through the second channel;
    determining a ratio of the third measurement to the second measurement; and
    determining a total flow volume of the fluid based on the first measurement and the determined ratio.

13. The method of claim 12, wherein the determining the total flow volume of the fluid based on the first measurement and the determined ratio includes determining the total flow volume of the fluid according to the following formula:

$$\text{Total Flow Volume} = X + X(Z/Y);$$

wherein:
X is the flow volume amount of the fluid based on the first measurement;
Y is the second measurement; and
Z is the third measurement.

14. The method of claim 12, further comprising:
    dividing the flow of the fluid at the input to the proportional flow device via a conditioning geometry disposed at the input such that the first portion of the fluid flows into the first channel and the second portion of the fluid flows into the second channel.

15. A proportional flow device for measuring fluid volume flow, comprising:
- a measurement channel, the measurement channel including:
  - a measurement device configured to obtain a primary measurement representative of a primary flow volume amount of a first portion of a fluid flowing through the measurement channel; and
  - a first flow comparison sensor configured to sense a first comparison measurement representative of a first comparison flow volume amount of the first portion of the fluid flowing through the measurement channel; and
- a bypass channel, the bypass channel including a second flow comparison sensor configured to sense a second comparison measurement representative of a second comparison flow volume amount of a second portion of the fluid flowing through the bypass channel,
- wherein a total flow volume amount of the fluid flowing collectively through the measurement channel and the bypass channel is determinable based on the primary measurement and a ratio of the second comparison measurement to the first comparison measurement.

16. The proportional flow device of claim 15, wherein the first flow comparison sensor and the second flow comparison sensor are each calibrated to be within a tolerance of accuracy in reference to each other.

17. The proportional flow device of claim 15, further comprising a processor, wherein the processor is configured to determine the total flow volume amount based on the following formula:

Total Flow Volume=$X+X(Z/Y)$;

wherein:
- X is the primary flow volume amount based on the primary measurement;
- Y is the first comparison measurement; and
- Z is the second comparison measurement.

18. The proportional flow device of claim 17, further including a housing, wherein the processor is located within the housing.

19. The proportional flow device of claim 17, further including a housing, wherein the processor is located external to the housing, and wherein the proportional flow device further comprises:
- a communications subsystem for providing measurement data to the processor over a network.

20. A method of measuring fluid flow in a proportional flow device through which a flow of fluid is divided among at least two flow channels, the method comprising:
- disposing a measurement device in a first channel of a proportional flow device;
- disposing a first flow comparison sensor in the first channel of the proportional flow device;
- disposing one or more additional flow comparison sensors in one or more respective additional channels of the proportional flow device, the additional channels acting as bypass channels in the proportional flow device, the first channel and the additional channels sharing an input;
- obtaining a first measurement from the measurement device in the first channel through which a first portion of a fluid is flowing, the first measurement representative of a flow volume amount of the fluid flowing through the first channel;
- obtaining a second measurement from the first flow comparison sensor in the first channel, the second measurement representative of a first comparison flow volume amount of the fluid flowing through the first channel;
- obtaining one or more third measurements from respective ones of the additional flow comparison sensors each disposed in its respective additional channel through which a respective additional portion of the fluid is flowing, each of the one or more third measurements representative of a respective comparison flow volume amount of the fluid flowing through its respective additional channel;
- determining respective ratios of each of the third measurements to the second measurement; and
- determining a total flow volume of the fluid based on the first measurement and the determined respective ratios.

* * * * *